United States Patent [19]

Atsumi et al.

[11] 4,332,806
[45] Jun. 1, 1982

[54] ANTITUMOR AND IMMUNOSUPPRESIVE 4-CARBAMOYL IMIDAZOLIUM-5-OLATE DERIVATIVES, PHARMACEUTICAL COMPOSITION AND PRODUCTION THEREOF

[75] Inventors: Toshio Atsumi, Kawanishi; Yoshiaki Takebayashi, Toyonaka; Takao Kiyohara, Takarazuka, all of Japan

[73] Assignee: Sumitomo Chemical Company, Limited, Osaka, Japan

[21] Appl. No.: 205,980

[22] Filed: Nov. 12, 1980

[30] Foreign Application Priority Data

Nov. 12, 1979 [JP] Japan ................ 54-146741

[51] Int. Cl.³ ................ A61K 31/415; C07D 233/90
[52] U.S. Cl. ................ 424/273 R; 548/337
[58] Field of Search ................ 548/337; 424/273 R

[56] References Cited

FOREIGN PATENT DOCUMENTS 50-121276 9/1975 Japan .
53-5162 1/1978 Japan .
53-53652 5/1978 Japan .

OTHER PUBLICATIONS

Mizuno et al., Journal of Antibiotics, vol. 27, No. 10 (1974) pp. 775-782.
Miller et al., J.A.C.S., vol. 74 (1952) pp. 2892-2894.
Sakaguchi et al., Journal of Antibiotics, vol. 28 (1975) pp. 798-803.
Tsujino et al., Proceeding of the First International Congress of IAMS, vol. 3 (1974) pp. 441-443.
Schipper et al., J.A.C.S., vol. 74 (1952), pp. 350-353.
Sakaguchi et al., Cancer Research, vol. 35 (1975) pp. 1643-1648.
Sakaguchi et al., Proceedings of the First International Congress of IAMS, vol. 3 (1974) pp. 539-541.

*Primary Examiner*—Richard Raymond
*Attorney, Agent, or Firm*—Wenderoth, Lind & Ponack

[57] ABSTRACT

There are provided compounds of the formula:

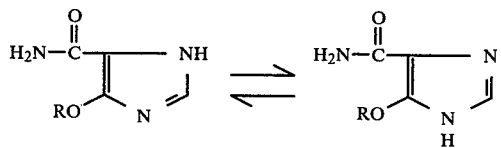

wherein R is an adamantoyl group substituted with a lower alkyl group, a lower alkoxy group, a hydroxy group, a lower alkanoyloxy group, an aroyloxy group, a halogen atom, an acetamido group, a nitro group, an azide group, a trifluoromethyl group or a phenyl group which may be substituted with a nitro group, a halogen atom, a lower alkyl group or a lower alkoxy group and a process producing them. These compounds are useful as antitumor agents and immunosuppressants.

9 Claims, No Drawings

ANTITUMOR AND IMMUNOSUPPRESIVE 4-CARBAMOYL IMIDAZOLIUM-5-OLATE DERIVATIVES, PHARMACEUTICAL COMPOSITION AND PRODUCTION THEREOF

The present invention relates to novel 4-carbamoylimidazolium-5-olate derivatives and preparation thereof. More particularly, the present invention pertains to 4-carbamoylimidazolium-5-olate derivatives useful as antitumor agents and immunosuppressants, a pharmaceutical composition containing at least one of them and a process for preparing them.

It has been known that the compound of the following formula (IV) has antitumor and immunosuppressive activity (Japanese Patent Publication (Kokai) No. 53-5162).

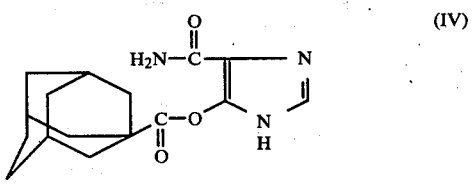

We have carried out an extensive study seeking new derivatives which have lower toxicity than the compound of the formula (IV), and have now found the novel imidazole derivatives of the present invention.

The novel imidazole derivatives of the present invention are those represented by the following formula (I),

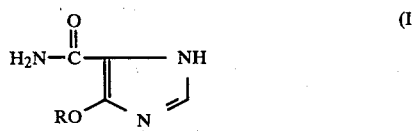

wherein R is an adamantoyl group substituted with a lower alkyl group, a lower alkoxy group, a hydroxy group, a lower alkanoyloxy group, an aroyloxy group, a halogen atom, an acetamido group, a nitro group, an azide group, a trifluoromethyl group or a phenyl group which may be substituted with a nitro group, a halogen atom, a lower alkyl group or a lower alkoxy group. That is, R is an adamantoyl group substituted with 1-3 of the above substituents. As used herein, the term "lower alkyl" means a straight or branched alkyl having 1 to 6 carbon atoms (e.g. methyl, ethyl, n-propyl, isopropyl, n-butyl, n-hexyl).

The term "lower alkoxy" means a straight or branched alkoxy having 1 to 6 carbon atoms (e.g. methoxy, ethoxy, n-propoxy, n-butoxy, isobutoxy, t-butoxy, n-hexyloxy).

The term "halogen" means fluorine, chlorine, bromine and iodine.

The term "lower alkanoyloxy" means a straight or branched alkanoyloxy having 2 to 6 carbon atoms (e.g. acetoxy, propionyloxy, pivaloyloxy).

The term "aroyloxy" means a benzoyloxy which may be substituted with a nitro group, a halogen atom, a lower alkyl group or a lower alkoxy group.

The compound of the formula (I) of the present invention can be prepared by reacting 4-carbamoylimidazolium-5-olate (II)

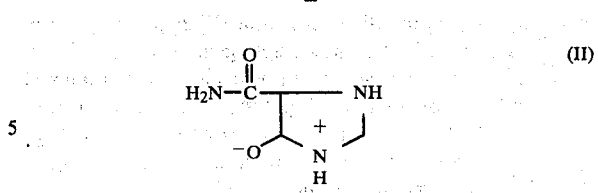

or its reactive derivative with a reactive derivative of a carboxylic acid of the formula (III)

R-OH (III)

wherein R is as defined above.

Examples of preferred reactive derivatives of carboxylic acids of the formula (III) are carboxylic acid halides (e.g. chlorides, bromides, iodides, fluorides), carboxylic acid anhydrides, mixed anhydrides (e.g. mixed anhydrides with ethyl chloroformate, isobutyl chloroformate and the like), activated esters (e.g. p-nitrophenyl ester, ester with N-hydroxysuccinimide), imidazolide (e.g. prepared by reacting N,N'-carbonyldiimidazole with carboxylic acids), activated intermediates prepared by reacting carboxylic acids with reaction products obtained from N,N-dimethylformamide and oxalyl chloride (or phosgene or thionyl chloride or phosphorus pentachloride) and the like.

Examples of preferred reactive derivatives of 4-carbamoylimidazolium-5-olate of the formula (II) are trimethylsilyl derivatives, trialkyltin derivatives, mercury salts, silver salts and the like.

Typical examples of preferred solvents which may be used in this reaction are methylene chloride, chloroform, pyridine, diethyl ether, tetrahydrofuran, dioxane, benzene, toluene, methanol, ethanol, N,N-dimethylformamide, formamide, N,N-dimethylacetamide, acetonitrile, nitromethane, acetone, and ethyl acetate.

The reaction can generally be effected by maintaining a reaction temperature from −78° to 100° C., preferably from 60° to 60° C.

The reaction of 4-carbamoylimidazolium-5-olate with carboxylic acid halides can usually be carried out in an inert polar solvent or a mixture of water and inert organic solvent, preferably in the presence of an inorganic or organic base at a temperature from −10° to 60° C. using one to two mole equivalents of the acid halide.

Typical examples of said inert polar solvent are tetrahydrofuran, dioxane, pyridine, N,N-dimethylformamide, formamide, N,N-dimethylacetamide and dimethylsulfoxide. Typical examples of said inert organic solvents are tetrahydrofuran, dioxane, diethyl ether, chloroform, dichloromethane, dichloroethane, benzene, toluene, and xylene. Examples of preferred inorganic base are sodium hydroxide, sodium carbonate, sodium bicarbonate, potassium carbonate or bicarbonate and potassium hydroxide. Examples of preferred organic base are pyridine, triethylamine and N,N-dimethylaniline.

The reaction of 4-carbamoylimidazolium-5-olate with activated intermediates prepared by reacting carboxylic acids with reaction products obtained from N,N-dimethylformamide and oxalyl chloride (or phosgene or thionyl chloride or phosphorus pentachloride) can usually be carried out in an organic solvent (e.g. acetonitrile, pyridine, N,N-dimethylformamide, N,N-dimethylacetamide, and chloroform) at a temperature from −78° to 80° C.

The compounds of the formula (I) can also be prepared by reacting a silylated derivative of 4-carbamoylimidazolium-5-olate with reactive derivatives of carboxylic acids (e.g. acid halides) at a temperature from −78° to 50° C. in an inert organic solvent (e.g. dimethylformamide, tetrahydrofuran, dioxane, diethylether, benzene, and toluene).

The silylated derivatives of 4-carbamoylimidazolium-5-olate are known and can be prepared by known methods (Hayashi, et al. Japanese Patent Publication (Kokai) No. 50-121276). When the compounds of the formula (I) exist in the form of their silylated derivative in the reaction mixture, the compounds of formula (I) can be obtained by a desilylated reaction with desilylated reagents (e.g. acetic acid, methanol, water).

When the reactive derivative of the acid (III) is an acid halide, the eliminated hydrogen halide can be neutralized by an organic base (e.g. triethylamine, pyridine).

The compounds of the formula (I) can be isolated and purified by known purification methods (e.g. recrystallization, column chromatography).

The imidazole derivatives of the present invention may exist in a mixture of the two tautomers as follows:

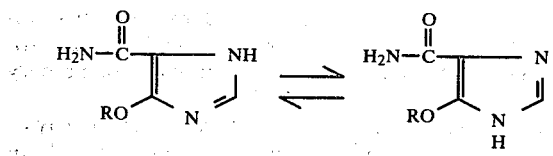

both of which are within the scope of the present invention.

The compounds of the present invention possess potent antitumor activities against Sarcoma 180, Lewis lung carcinoma, Ehrlich carcinoma, P-388 leukemia and the like. The compounds of the formula (I) are useful as antitumor agents and they exhibit particularly excellent inhibitory effects against tumors and exhibit a prolongation effect on the life span.

The antitumor activities of the compounds of the present invention were estimated according to the methods described in "Cancer chemotherapy reports" Part 3, Vol. 3, (No. 2) p. 13 (1972). The results are given in the following Table 1.

TABLE 1

Antitumor effect on experimental tumors in mice

| Compound | Dose (mg/kg) Route i.p. | Schedule | Inhibition Ratio (%) Lewis lung carcinoma (solid) |
|---|---|---|---|
| 5-Carbamoyl-1H-imidazole-4-yl 3'-bromoadamantane-1'-carboxylate | 100 | 5q2d | 66.2 |
| 5-Carbamoyl-1H-imidazole-4-yl 3'-chloroadamantane-1'carboxylate | 100 | 5q2d | 71.1 |
| 5-Carbamoyl-1H-imidazole-4-yl 3'-phenyladamantane-1'-carboxylate | 100 | 5q2d | 85.7 |
| 5-Carbamoyl-1H-imidazole-4-yl 3'-fluoroadamantane-1'-carboxylate | 100 | 5q2d | 65 |
| 5-Carbamoyl-1H-imidazole-4-yl 3',5',7'-trimethyl-adamantane-1'-carboxylate | 100 | 5q2d | 90 |

For determining antitumor activities, $BDF_1$ male mice, 5 weeks old, weighing between 18 and 22 grams were used. Each test group was composed of 6 to 7 mice. Two million cells of Lewis Lung Carcinoma were injected in the hind leg. The drug was administered intraperitoneally at day 1, 3, 5, 7 and 9 (or 5q2d).

After killing the mice at day 13, tumors were removed and weighed. The tumor inhibitory ratio was calculated according to the following formula.

$$\text{Inhibition ratio} = \left(1 - \frac{\text{the mean tumor weights of treated group}}{\text{the mean tumor weights of control group}}\right) \times 100$$

The compounds of the present invention also possess excellent immunosuppressive activity as well as potent antitumor activity.

The compounds (I) of the present invention have lower toxicity than the compound (IV) above, as shown in the following Table 2.

TABLE 2

Acute toxicities

| Compound | $LD_{50}$ (mg/kg) |
|---|---|
| 5-Carbamoyl-1H-imidazole-4-yl 3'-bromoadamantane-1'-carboxylate | 670–1000 |
| 5-Carbamoyl-1H-imidazole-4-yl 3'-chloroadamantane-1'-carboxylate | >1000 |
| 5-Carbamoyl-1H-imidazole-4-yl 3'-fluoroadamantane-1'-carboxylate | 670–1000 |
| 5-Carbamoyl-1H-imidazole-4-yl 3',5',7'-trimethyladamantane-1'-carboxylate | 670–1000 |
| 5-Carbamoyl-1H-imidazole-4-yl adamantane-1'-carboxylate (Compound (IV)) | 250–297 |

For determining acute toxicities ICR male mice, 5 weeks old, were used. The drug was administered intraperitoneally.

The compounds of the present invention can be administered orally or parenterally to warm-blood animals at a daily dose of 2–200 mg/kg as an antitumor agent, and 1–100 mg/kg as an immunosuppressant, in a conventional dosage unit form.

The compounds of the present invention are made up alone or together with a conventional pharmaceutical carrier or diluent into a conventional solid or liquid pharmaceutical preparation (e.g. powders, granules, tablets, capsules, suspensions, emulsions, and solutions) using the conventional methods in the pharmaceutical field. For example, tablets or capsules contain 50–500 mg of compounds (I).

The following examples are giving to illustrate the present invention more precisely but it is not intended to limit the present invention thereto.

EXAMPLE 1

To a suspension of 0.98 g. of 4-carbamoylimidazolium-5-olate in 20 ml. of dry pyridine was added 2.17 g. of 3-fluoroadamantane-1-carbonylchloride, and the reaction mixture was stirred for an hour at 40°–45° C. Then the reaction mixture was concentrated under reduced pressure. To the residue was added ethylacetate and water and then separated crystals were filtered off, washed with ethyl acetate and dried to give 2.07 g. of 5-carbamoyl-1H-imidazole-4-yl 3'-fluoroadamantane-1'-carboxylate.

The crude material was recrystallized from methanol and water.

m.p.: 199° C. (dec.).

$v_{max}^{nujol}$ (cm$^{-1}$): 3530, 3420, 3140, 3080, 2690, 1760, 1680, 1595, 1580, 1425, 1205, 1110, 990.

EXAMPLE 2

Following a procedure similar to that of Example 1 but using 0.89 g. of 4-carbamoylimidazolium-5-olate, 18 ml. of dry pyridine and 1.96 g. of 3-chloroadamantane-1-carbonyl chloride there was obtained 1.7 g. of 5-carbamoyl-1H-imidazole-4-yl 3'-chloroadamantane-1'-carboxylate.

The crude material was recrystallized from N,N-dimethylformamide and water.

m.p.: 192.5° C. (dec.).

$v_{max}^{nujol}$ (cm$^{-1}$): 3480, 3170, 1770, 1600, 1605, 1180, 1020.

EXAMPLE 3

Following a procedure similar to that of Example 1 but using 0.83 g. of 4-carbamoylimidazolium-5-olate, 17 ml. of dry pyridine and 2.17 g. of 3-bromoadamantane-1-carbonyl chloride there was obtained 1.5 g. of 5-carbamoyl-1H-imidazole-4-yl 3'-bromoadamantane-1'-carboxylate.

The crude material was recrystallized from N,N-dimethylformamide and water.

m.p.: 187.5° C. (dec.).

$v_{max}^{nujol}$ (cm$^{-1}$): 3480, 3170, 1775, 1660, 1605, 1180, 1100, 1020.

EXAMPLE 4

Following a procedure similar to that of Example 1 but using 0.89 g. of 4-carbamoylimidazolium-5-olate, 18 ml. of dry pyridine and 2.31 g. of 3-phenyladamantane-1-carbonyl chloride there was obtained 2.5 g. of 5-carbamoyl-1H-imidazole-4-yl 3'-phenyladamantane-1'-carboxylate.

The crude material was recrystallized from N,N-dimethylformamide and water.

m.p.: 190° C. (char.).

$v_{max}^{nujol}$ (cm$^{-1}$): 3475, 3150, 1780, 1660, 1615, 1180, 1110, 1040, 1020.

EXAMPLE 5

Following a procedure similar to that of Example 1 but using 2.3 g. of 3-methoxyadamantane-1-carbonyl chloride there was obtained 1.33 g. of 5-carbamoyl-1H-imidazole-4-yl 3'-methoxyadamantane-1'-carboxylate.

$v_{max}^{nujol}$ (cm$^{-1}$): 3480, 3180, 1770, 1660, 1605, 1195, 1040.

EXAMPLE 6

To a suspension of 0.636 g. of 4-carbamoylimidazolium-5-olate in 20 ml. of dry pyridine was added 1.445 g. of 3,5,7-trimethyladamantane-1-carbonyl chloride at room temperature. After being stirred for two hours at 40°–45° C., the reaction mixture was cooled to room temperature and 0.93 ml. of triethylamine was added. After being stirred for half an hour, separated crystals were filtered off and the filtrate was concentrated under reduced pressure. To the residue was added dry diethyl ether and then separated crystals were filtered off and dried to give 1.506 g. of 5-carbamoyl-1H-imidazole-4-yl 3',5',7'-trimethyladamantane-1'-carboxylate.

The crude material was purified by silica gel column chromatography and subjected to recrystallization from dimethylsulfoxide and diethyl ether.

m.p.: 206°–207° C.

$v_{max}^{nujol}$ (cm$^{-1}$): 1755.

Elemental analysis:

| Calculated for $C_{18}H_{25}N_3O_3 \cdot \frac{1}{2}H_2O$ | C (%) | H (%) | N (%) |
|---|---|---|---|
|  | 64.07 | 7.67 | 12.45 |
| Found | 64.02 | 7.62 | 12.38 |

According to the present invention, there are obtained, for example, the following compounds:

5-Carbamoyl-1H-imidazole-4-yl 3'-hydroxyadamantane-1'-carboxylate.

5-Carbamoyl-1H-imidazole-4-yl 3'-acetoxyadamantane-1'-carboxylate.

5-Carbamoyl-1H-imidazole-4-yl 3'-benzoyloxyadamantane-1'-carboxylate.

5-Carbamoyl-1H-imidazole-4-yl 3'-acetamidoadamantane-1'-carboxylate.

5-Carbamoyl-1H-imidazole-4-yl 3'-nitroadamantane-1'-carboxylate.

5-Carbamoyl-1H-imidazole-4-yl 3'-azideadamantane-1'-carboxylate.

5-Carbamoyl-1H-imidazole-4-yl 3'-trifluoromethyladamantane-1'-carboxylate.

5-Carbamoyl-1H-imidazole-4-yl 3'-(p-nitrophenyl)adamantane-1'-carboxylate.

5-Carbamoyl-1H-imidazole-4-yl 3'-(p-chlorophenyl)adamantane-1'-carboxylate.

5-carbamoyl-1H-imidazole-4-yl 3'-(p-tolyl)adamantane-1'-carboxylate.

5-Carbamoyl-1H-imidazole-4-yl 3'-(p-methoxyphenyl)adamantane-1'-carboxylate.

5-Carbamoyl-1H-imidazole-4-yl 3'-(p-nitrobenzoyloxy)adamantane-1'-carboxylate.

5-Carbamoyl-1H-imidazole-4-yl 3'-(p-chlorobenzoyloxy)-adamantane-1'-carboxylate.

5-Carbamoyl-1H-imidazole-4-yl 3'-(p-methylbenzoyloxy)adamantane-1'-carboxylate.

5-Carbamoyl-1H-imidazole-4-yl 3'-(p-methoxybenzoyloxy)adamantane-1'-carboxylate.

What is claimed is:

1. A compound of the formula

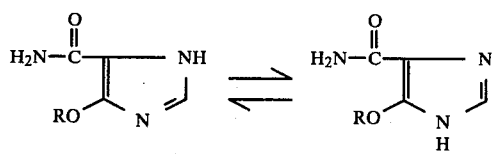

wherein R is adamantoyl substituted with 1–3 substituents selected from the group consisting of lower alkyl, lower alkoxy, hydroxy, lower alkanoyloxy, aroyloxy, halogen, acetamido, nitro, an azide group, trifluoromethyl, or phenyl which may be substituted with nitro, halogen, lower alkyl or lower alkoxy.

2. A compound according to claim 1, wherein R is 3-fluoroadamantanecarbonyl.

3. A compound according to claim 1, wherein R is 3-chloroadamantanecarbonyl.

4. A compound according to claim 1, wherein R is 3-bromoadamantanecarbonyl.

5. A compound according to claim 1, wherein R is 3-phenyladamantanecarbonyl.

6. A compound according to claim 1, wherein R is 3,5,7-trimethyladamantanecarbonyl.

7. A compound according to claim 1, wherein R is 3-methoxyadamantanecarbonyl.

8. An antitumor composition which comprises an antitumor effective amount of a compound of claim 1 as an active ingredient and a pharmacetically acceptable carrier or diluent.

9. An immunosuppressant composition which comprises an immunosuppressive amount of a compound of claim 1 as an active ingredient and a pharmaceutically acceptable carrier or diluent.

* * * * *